United States Patent [19]

Vantard et al.

[11] Patent Number: 4,623,450
[45] Date of Patent: Nov. 18, 1986

[54] ARTIFICIAL KIDNEY

[75] Inventors: Georges Vantard, Champs sur Marne; Gilbert Clement, Bonville; Jean-Pierre Vasseur, Longjumeau, all of France

[73] Assignee: Hospal Industrie, Meyzieu, France

[21] Appl. No.: 763,060

[22] Filed: Aug. 6, 1985

Related U.S. Application Data

[63] Continuation of Ser. No. 387,225, Jun. 10, 1982, abandoned.

[30] Foreign Application Priority Data

Jun. 16, 1981 [FR] France .............................. 81 11985

[51] Int. Cl.$^4$ ............................................. B01D 13/00
[52] U.S. Cl. ...................................... 210/87; 210/90; 210/96.2; 210/34.3
[58] Field of Search ................ 210/321.3, 87, 90, 96.2

[56] References Cited

U.S. PATENT DOCUMENTS

3,774,762 11/1973 Lichtenstein ................ 210/321.3 X

Primary Examiner—Frank Spear
Attorney, Agent, or Firm—Gerald D. Sharkin; Robert S. Honor; Walter F. Jewell

[57] ABSTRACT

An artificial kidney comprising a haemodialyser (a) associated with and preferably integrated into a common unit D adapted to be connected simultaneously to a patient P, to a container 34 of fresh and/or used dialysis liquid, and to a controlling and checking console (h). The disposable common unit can perform all the functions necessary for a treatment. These functions are not performed by self-contained members, but by a small number of flexible multifunctional parts, such as elements 14 and 15, each cooperating with rigid parts such as parts 10, 11, 12 and 13.

7 Claims, 12 Drawing Figures

ARTIFICIAL KIDNEY

This is a continuation of application Ser. No. 387,225, filed June 10, 1982, now abandoned.

The present invention relates to an artificial kidney.

Certain types of artificial kidneys in current use comprise, in particular, a disposable haemodialyser and disposable elements constituting an extracorporal circuit through which the blood passes. For the purpose of simplifying the manufacture of these devices, reducing their cost and facilitating their use, it has been proposed to incorporate, into the haemodialyser, certain elements of the circuit through which the blood passes, thus forming a single disposable unit around the haemodialyser.

Still with the same purpose of simplification and cost reduction, it has recently been proposed to associate, with each haemodialyser, a set of preassembled disposable elements constituting all or part of the circuit through which the dialysis liquid passes, and disposable elements making it possible to remove and measure the desired amounts of ultrafiltrate. Thus, an artificial kidney is available which consists essentially of a plurality of disposable self-contained elements which each perform a particular function and which are connected to one another.

Artificial kidneys of this type represent a real improvement over the artificial kidneys of the prior art, but there still remains the need to have constantly available artificial kidneys which are very economical to manufacture, assemble and transport, and which are easier to use and more reliable.

It is therefore an object of the present invention to provide an artificial kidney of compact simplified construction, which involves fewer components and less material and is hence substantially more economical.

Another object of the present invention is an artificial kidney in which the hydraulic circuits through which pass, in particular, the blood, the dialysis liquid and, where appropriate, the ultrafiltrate are independent of the controlling and checking members, thus ensuring improved safety and ease of construction and use.

A further object of the present invention is an artificial kidney of low weight and low bulk, so that it is easier to transport, store and use.

A still further object of the present invention is an artificial kidney which substantially reduces manipulations and possible errors, which eliminates risks which can arise during sterilisation and which is thus at one and the same time rapid, safe, simple and economical to use, as well as being particularly suitable for dialysis at home.

According to the present invention there is provided an artificial kidney comprising, in combination, the following elements:

(a) a haemodialyzer including:
  (i) a membrane which is capable of permitting the treatment of blood, particularly by dialysis and by ultrafiltration, said membrane dividing the haemodialyzer into first and second compartments;
  (ii) means for feeding blood to and from the first compartment; and
  (iii) means for feeding the dialysis liquid to and from the second compartment;

(b) an extracorporal circuit through which the blood passes outside the haemodialyzer from the patient to the blood feeding means of the haemodialyzer;

(c) means for preparing the dialysis liquid, ready for circulation through said second compartment;

(d) means for causing the dialysis liquid to circulate through said second compartment;

(e) means for regulating the pressure of the dialysis liquid in said haemodialyzer;

(f) storage means for storing the fresh and/or used dialysis liquid;

(g) means for removing and measuring amounts of dialysis liquid equal to the desired amounts of ultrafiltrate and (h) means for controlling and checking, in particular, the elements (b) and (d), wherein the elements (b) and (d) are at least partially integrated into a disposable common unit which essentially comprises rigid or semi-rigid multifunctional elements disposed on each side of one or more independent flexible elements which perform sealing and/or storage functions.

The present invention is not based on an attempt to find the best possible way of assembling all the components required to carry out the desired functions, but, on the contrary, is based on an attempt to reduce the number of self-contained elements by incorporating different elements, each having at least one particular function, into a common unit.

According to the invention, this problem is solved by at least partial integration of the means constituting the extracorporal blood circuit through which the blood passes from the patient to and from the haemodialyser, and also of the means of circulating the dialysis liquid.

The term "integration" understood here as meaning the use of multifunctional elements which are common to at least two different members and which have a particular function in each of these members. These functions can be either of the same type or of a different type.

The term "total integration" understood as meaning a unit grouping together various members consisting exclusively of multifunctional elements.

The term "partial integration" understood as meaning either a unit consisting of members of which only some have one or more multifunctional elements in common, or a unit consisting of members which only partially consist of multifunctional elements, or also a unit consisting of a combination of the previous two cases.

Furthermore, as the haemodialysers have hitherto benefitted from numerous and significant improvements brought about by mass production, and since the equipment, the function of which is in particular to prepare the dialysis liquid, store it and cause it to circulate, and to check the ultrafiltrate, has only developed, by contrast, to a relatively small extent, a substantial technological imbalance has resulted. The present invention thus proposes to transfer the greatest possible member of elements of this equipment to a disposable unit, most frequently constructed around the haemodialyser, so that it benefits from mass-production technology. The equipment can thus be considerably lightened in weight and simplified through the extended use of consumable, generally disposable materials.

It will become clearly apparent from the description which now follows that, since the dialysis circuit of an artificial kidney consists of a plurality of members each ensuring very particular functions, the integration of two or more of these members into a common unit can lend itself to a multiplicity of solutions, firstly because of the type and number of the integrated members and secondly because of the choice of the technological solution selected for carrying out this integration.

The invention will be more easily understood from following description, which is given merely by way of example, reference being made to the accompanying drawings, which show, diagrammatically and with no fixed scale, various embodiments of the invention and the prior art. In the various figures, the same numbers will denote identical or equivalent members. In the drawings:

Figure 1:
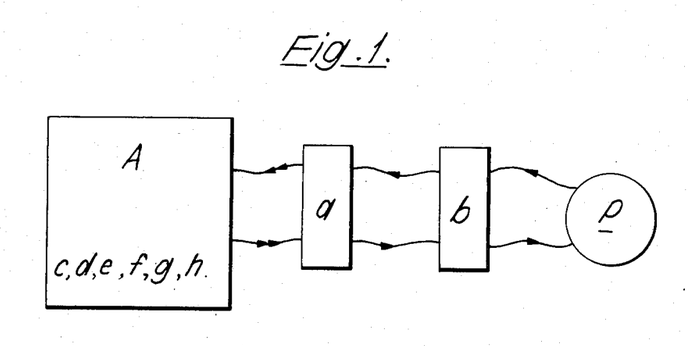
FIG. 1 is a diagrammatical view of one form of prior art artificial kidney.

The principal means constituting an artificial kidney according to the prior art are shown diagrammatically in FIG. 1. The patient P is connected to a haemodialyser (a) by lines through which the blood passes and which contain different members, such as a circulating pump, filter, bubble trap, and so on, which are indicated diagrammatically by the rectangle (b). The haemodialyser (a) itself is connected to an apparatus (A) comprising the means (c) for preparing the dialysis liquid, the pump (d) for causing the dialysis liquid to circulate, means (e) for regulating the pressure of the dialysis liquid in the haemodialyser, storage means (f) for storing fresh and-/or used dialysis liquid, removal means (g) for removing and measuring amounts of liquid equal to desired amounts of ultrafiltrate and control means (h) for controlling and checking, in particular, parts (b) and (d).

Figure 2:
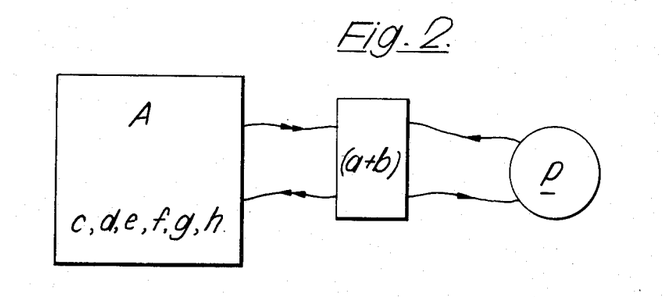
FIG. 2 is a diagrammatical view of a second form of artificial kidney according to the prior art.

The apparatus (A) is re-usable after each treatment, after first being sterilised. The haemodialyser (a) and the blood lines (b) are on the contrary generally disposable. Thus, their grouping together by integration into a common unit (a+b), as shown in FIG. 2, has already been contemplated.

Figure 3:
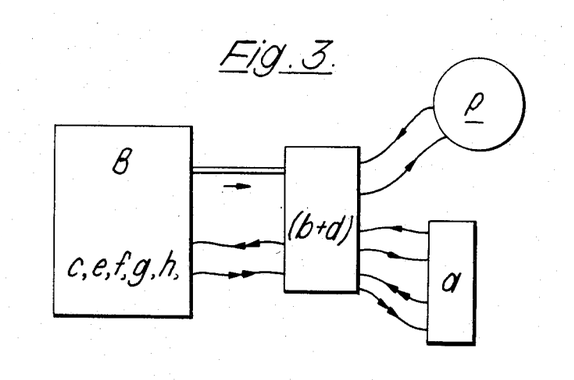
FIGS. 3, 4 and 5 are diagrammatical views of three embodiments of artificial kidney according to the present invention.

Unlike the closest prior art doctrine, according to the present invention (see FIG. 3), a common unit is composed of all the circuits through which the blood (b) and the dialysis liquid (d) flow, outside the haemodialyser, these circuits being in addition at least partially integrated with one another, that is to say materially composed, at least in part, of common multifunctional elements. The common unit grouping together the means (b+d) is designed to be disposable. In addition, it is connected on the one hand to the patient P and on the other hand to the haemodialyser (a), and finally to the simplified re-usable apparatus B, which now consists only of the parts (c), (e), (f), (g) and (h).

Figure 4:
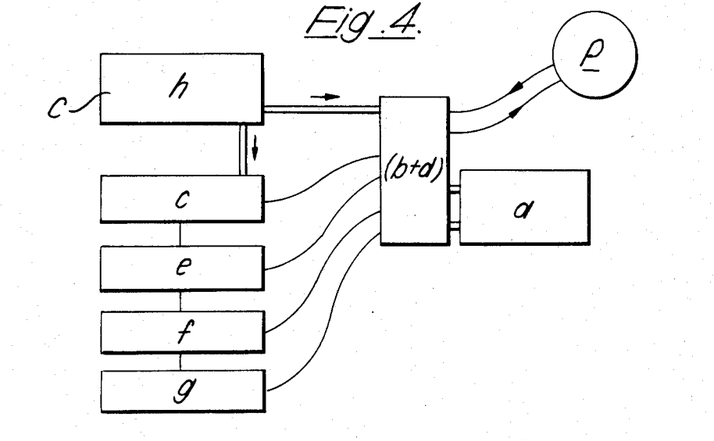

As will be seen later on, the present invention lends itself to a multiplicity of embodiments, such as that illustrated as an example in FIG. 4. It will in particular be observed that the haemodialyser (a) is disposed side by side with the common unit (b+d), that is to say it is connected directly to the said unit by short, rigid and preferably easily lockable connections. It will in addition be noted that the controlling and checking members (h) are grouped together in a casing (C) into the interior of which neither the blood circuit nor the dialysis liquid circuit extends. This casing groups together only electrical, mechanical or electronic members, together with auxiliary hydraulic circuits where applicable, and this arrangement constitutes an important simplification and offers improved safety in use. The parts (c), (e), (f) and (g) may be self-contained and they are connected to one another, to the common unit (b+d) and, where applicable, to the control casing C.

Figure 5:
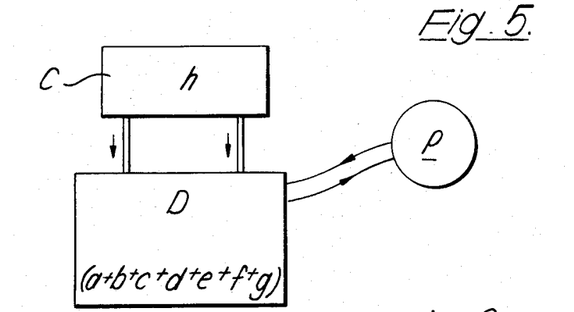

In FIG. 5 a disposable common unit D can group together all the parts (a), (b), (c), (d), (e), (f) and (g). These parts are at least partially integrated with one another. In order to make up the artificial kidney according to the invention, it will be sufficient to connect the common unit D to the re-usable casing C grouping together the controlling and checking members, and to utilise this kidney it will be sufficient to connect the common unit D to the patient P.

Figure 6:
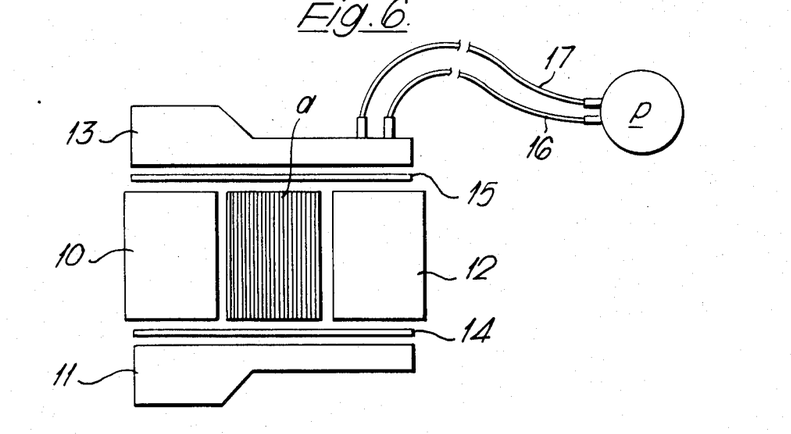
FIG. 6 is a diagrammatical view of one embodiment of the disposable common unit of FIG. 5.

It is this preferred embodiment that will now be described in greater detail. Thus, FIG. 6 shows diagrammatically a common unit D, which may comprise the parts (a), (b), (c), (d), (e), (f) and (g) and which is capable of performing all the corresponding functions. It is composed of a haemodialyser (a) of the flat membrane type, cooperating with four rigid multifunctional elements 10, 11, 12 and 13 and two flexible multifunctional elements 14 and 15 which are separate and independent of one another. It can be connected to the patient P by two simple flexible tubes 16 and 17 for the circulation of the blood, which are not provided with any particular device.

Figure 7:
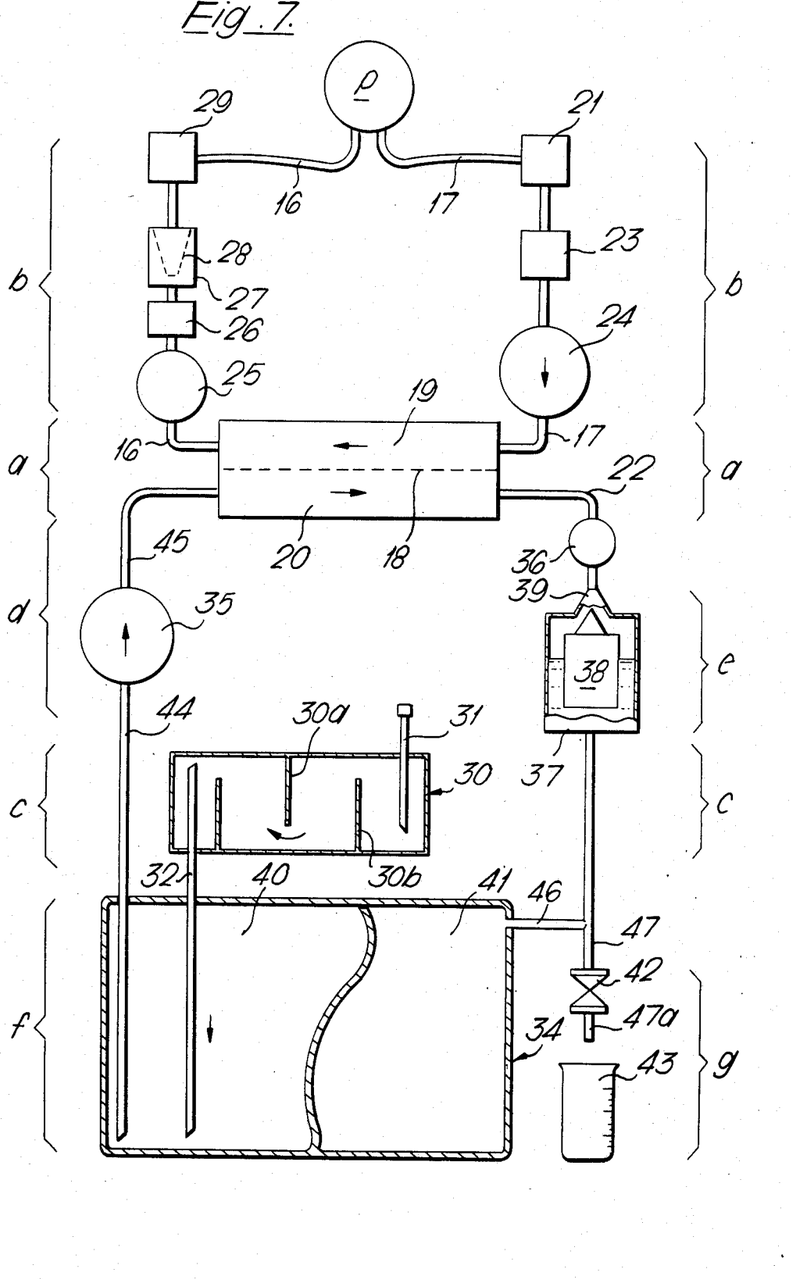
FIG. 7 is the schematic diagram of one example of the circuits through which the blood and the dialysis liquid flow and which can be at least partially integrated into a common unit of the type illustrated in FIGS. 5 or 6.

FIG. 7 illustrates diagrammatically and in detail an example in which the different parts (a), (b), (c), (d), (e), (f) and (g) can be grouped together and at least partially integrated into a common unit D according to FIGS. 5 and 6, together with their connections.

Thus, the haemodialyser (a) includes a membrane 18 permitting the treatment of the blood, particularly by dialysis and by ultrafiltration, and dividing the compartment into two compartments 19 and 20, the blood flowing through the first compartment and the dialysis liquid through the second.

The part (b) constituting the extracorporal circuit through which the blood flows outside the haemodialyser comprise an arterial tube 17 and a venous tube 16 connected directly to the patient; inside the common unit D these tubes carry in succession a series of devices, each of which performs a specific function known per se. These devices comprise for example, on the arterial branch 17, a blood inlet spigot, an injection zone 23 enabling injections of serum to be made if required, a blood circulation pump 24, and, on the venous branch 16, means 25 for measuring the pressure of the blood, an injection zone 26, a bubble trap 27, a blood filter 28 and an outlet spigot 29.

The means (c) for preparing the dialysis liquid comprise essentially a reservoir 30 which initially contains a concentrated solution of dialysis liquid, the volume of which corresponds exactly to the dialysis liquid capacity of the entire circuit, so that the use of a conductivity meter becomes unnecessary. A tube 31 permits the introduction of water, which is generally first brought to a temperature between 37° and 40° C. and softened. A dip tube 32 connects the top part of the reservoir 30 to the bottom of a storage container 34.

Baffles 30a and 30b may assist the regular displacement of the concentrate by the water.

The part (d) comprises essentially a circulating pump 35 for the dialysis liquid and also connection tubes 44 and 45 between, on the one hand, a fresh dialysis liquid storage compartment 40 and the haemodialyser and, on the other hand, tubes 22 and 46 between the haemodialyser and the used dialysis liquid storage compartment 41. The part (d) comprises accessories normally provided in such a circuit, for example, on the tube 22, a transparent portion 36 which cooperates with a colorimeter (not shown) disposed on the console (h). It could obviously optionally include a conductivity meter and-/or means for preheating the dialysis liquid.

The means (e) for regulating the pressure of the dialysis liquid in the haemodialyser are composed, in the example described, of a chamber 37 containing a float 38, the top of the float cooperating with the inlet orifice 39 of the chamber for the purpose of automatically regulating, in a manner known per se, the pressure of the dialysis liquid in the haemodialyser.

The part (f) comprises, inside an advantageously heat-insulated storage container 34, a leaktight, deformable, supple plastic bag which is initially devoid of air and is capable of occupying a volume equal to the internal volume of the container. This bag is divided into two complementary compartments 40 and 41. The compartment 40 is connected to the concentrate reservoir 30 by the dip tube 32 and to the pump 35 by a tube 44; it contains the fresh dialysis liquid. The compartment 41 is connected to the tank 37 by the tube 46, from which it receives the used dialysis liquid.

The means (g) comprise for example a device 42 for obturating a tube 47 connected to float chamber 37 and a graduated vessel 43 making it possible to remove and to measure, in a manner known per se, amounts of liquid, essentially used dialysis liquid, equal to the desired amounts of ultrafiltrate to be removed from the patient.

Figure 8:
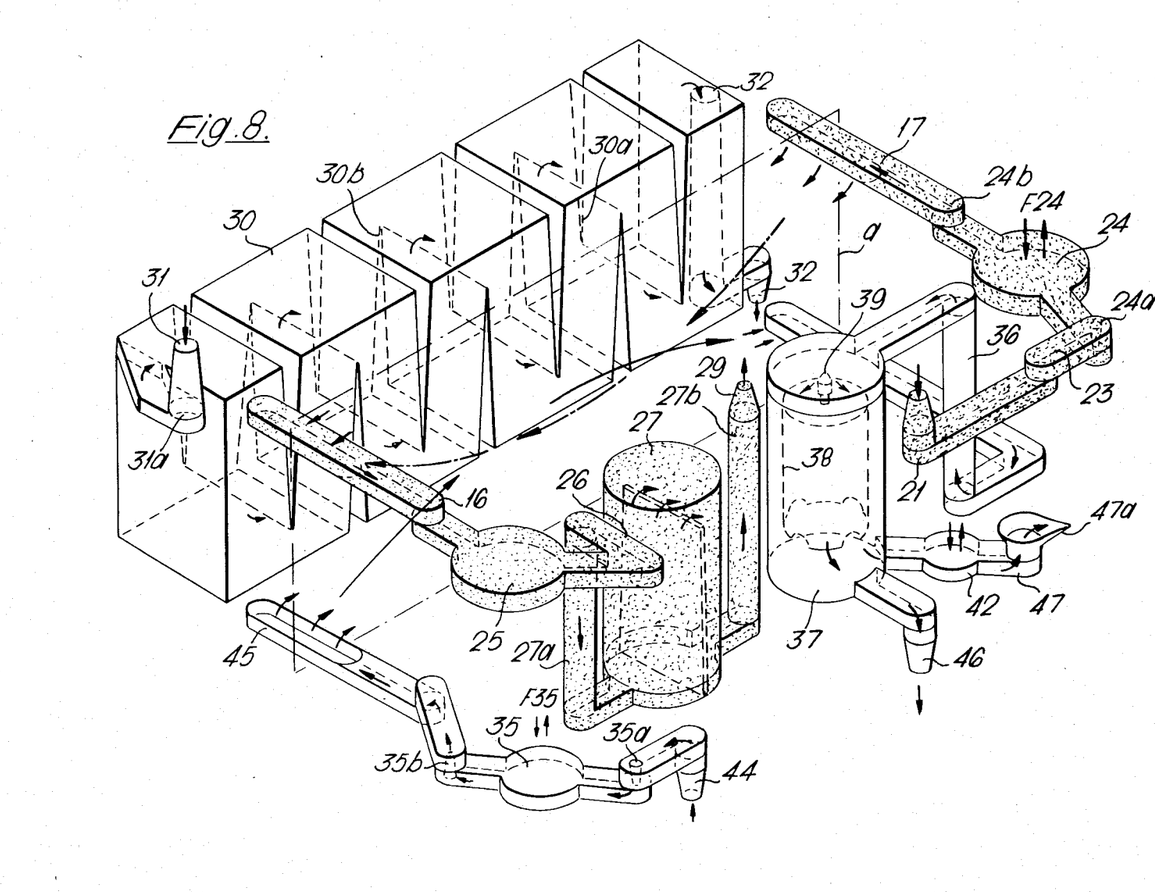
FIG. 8 is a perspective view of the circuits through which the blood and the dialysis liquid flow, and which are shown in FIG. 7 and effectively constitute the common unit.
Figure 10:
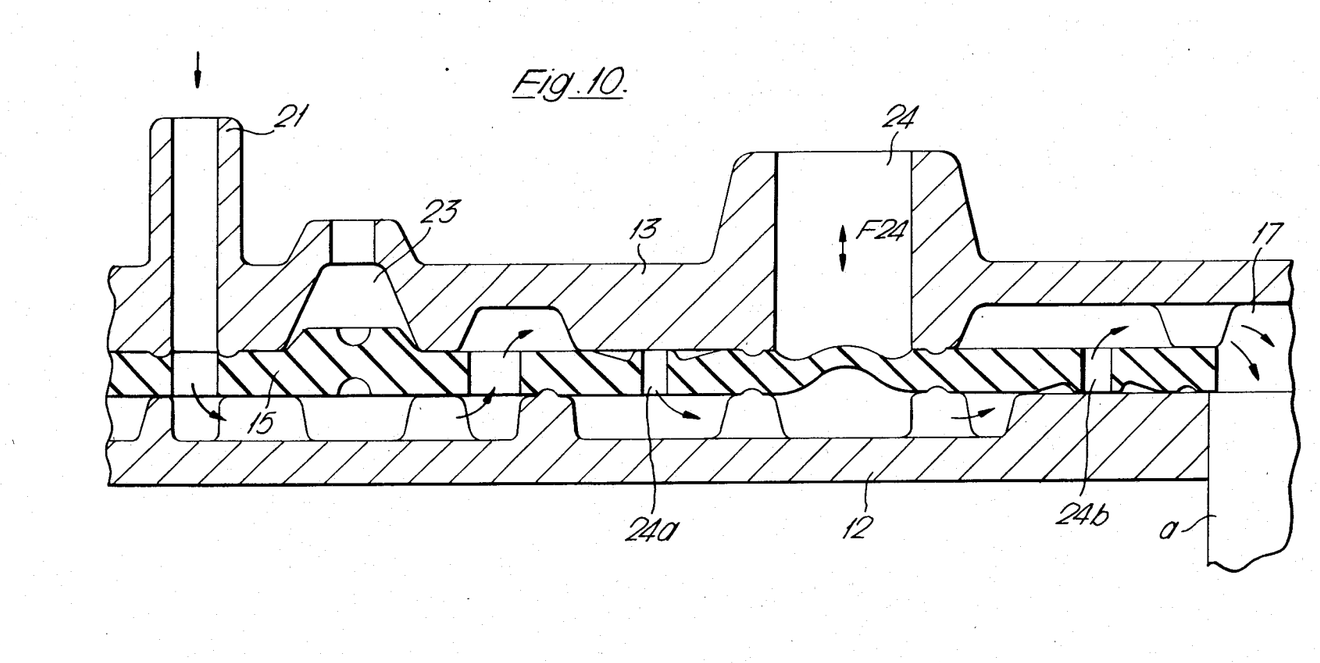
FIG. 10 is a scrap section on the line X—X of FIG. 9.

Referring now to FIGS. 8 and 10, it will be seen that the arterial blood passes through a blood inlet spigot 21, through the injection zone 23 permitting injections of serum, and then reaches the circulating pump 24, which is for example of the plane membrane type known per se, whose reciprocating movement is controlled pneumatically or mechanically in accordance with the arrows F 24 by a motor (not shown) included in the console (h). The pump 24 is disposed between two non-return diaphragm valves 24a and 24b, which are likewise of types known per se. The blood is thus pumped into the arterial tube 17 towards a top end of the haemodialyser (a), which in FIG. 8 is represented diagrammatically by a rectangle in perspective.

The blood passes out of the opposite top end of the haemodialyser by way of the venous tube 16, passes under the membrane in a zone 25 which can be connected to a pressure gauge or to a force pickup of a type known per se, which is housed on the console (h), passes through an injection zone 26, and then by way of a tube 27a reaches a bubble trap 27 of a type known per se, which contains means for adjustment to atmospheric pressure and, at its base, a blood filter of a conventional type (the said means and the said filter not being shown). By way of the tube 27b the blood finally reaches the outlet spigot 29, from which it returns to the patient.

The concentrated solution of dialysis liquid is stored in the reservoir 30, which is divided into compartments by a series of alternating vertical baffles 30a and 30b. The water, after preheating and softening, is introduced through the tube 31 and passes through a non-return valve 31a similar to the valve 24a of the pump 24. The mixture of water and concentrated solution is evacuated through the dip tube 32 (partly shown) into the compartment 40 of the storage container 34 (see FIG. 7).

The fresh dialysis liquid is taken from this compartment 40 via the tube 44 by means of a plane diaphragm pump 35 of a type known per se, similar to the pump 24, whose reciprocating movement is controlled in accordance with the arrows F 35 by a motor (not shown) included in the console (h). The pump is disposed between two non-return valves 35a and 35b, similar to the valves 24a and 24b. The dialysis liquid is thus pumped back through the pipe 45 to a bottom end of the haemodialyser (a), through which it passes countercurrently to the blood. It passes out at the opposite bottom end of the haemodialyser, then passing through a transparent tube 36 cooperating with a colorimeter (not shown) housed in the console (h), thus reaching the orifice 39 of the float chamber 37 containing the float 38. The tube 46 returns the used dialysis liquid to the compartment 41.

With the aid of the obturation device 42, the tube 47 makes it possible to collect a volume of liquid equal to the desired volume of ultrafiltrate which flows off through the pouring spout 47a into a graduated vessel 43.

Figure 9:
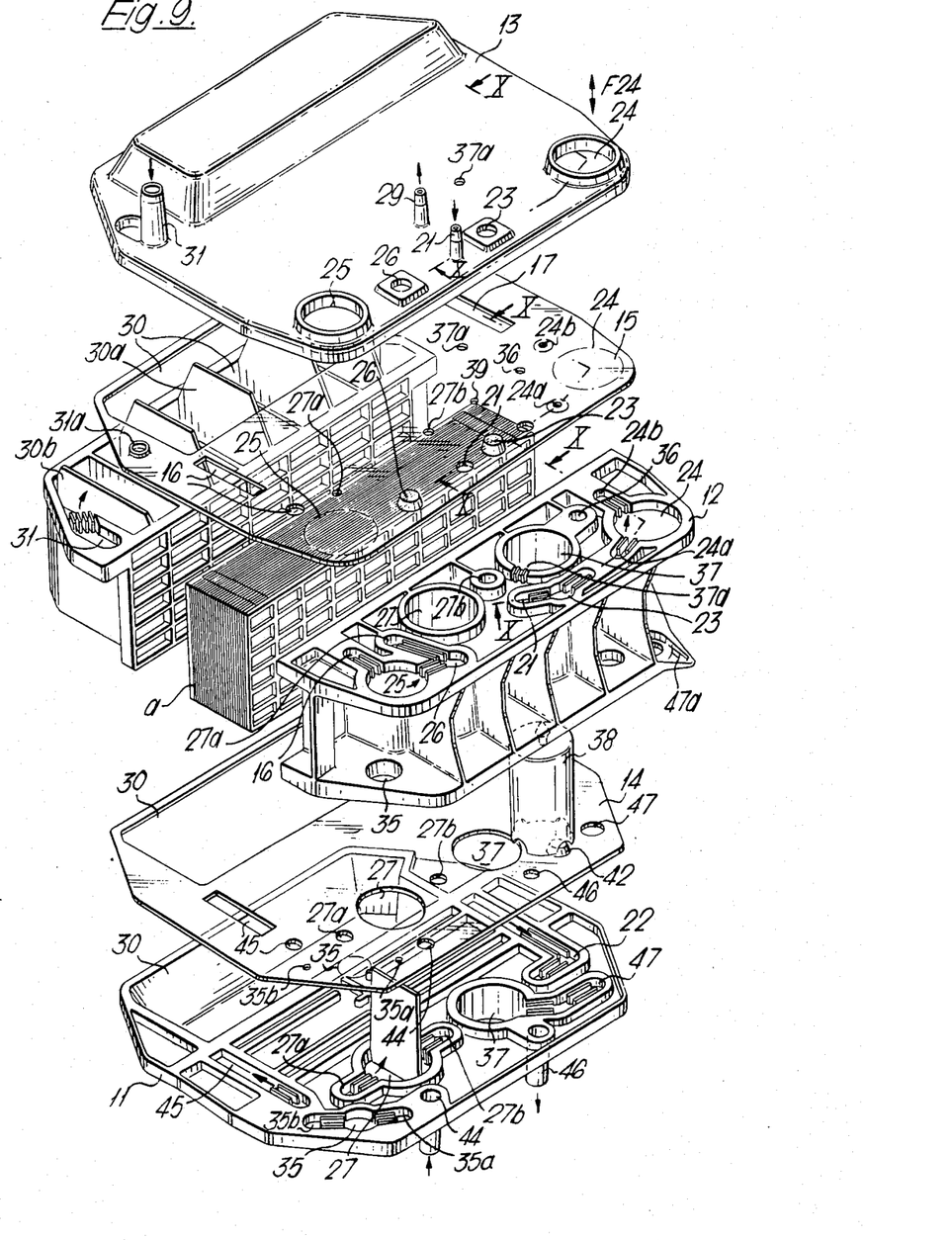
FIG. 9 is an exploded view in perspective of the common unit of the type shown diagrammatically in FIG. 6, wherein the different elements form the circuits shown in perspective in FIG. 8.

The haemodialyser (a) shown in FIG. 9 is composed in a manner known per se of a stack of intercalated plates and plane membranes folded around these intercalated plates. The latter are formed as solid plates or of perforated lattices.

The flexible elements 14 and 15 serve in particular the functions of sealing, in contact with the dialysis liquid and the blood respectively, both in the haemodialyser and outside the latter.

The rigid or semirigid elements 10, 11, 12 and 13 together serve a function of retention in relation to the stack of intercalated plates and membranes constituting the haemodialyser. Thus, the haemodialyser (a) is first clamped between the side elements 10 and 12, either to a constant size or with constant pressure, whereupon, while these elements are held in place, the flexible elements 14 and 15 are placed in position, followed by the elements 11 and 13, which are joined for example by ultrasonic welding to the elements 10 and 12.

It will thus be realised that the assembly of the common unit D according to the invention is reduced to the simple mounting of the end plates and side plates of a haemodialyser. This is a remarkable advantage in view of the very numerous additional functions performed by the common unit D in comparison with a conventional haemodialyser.

The bottom multifunctional element 11 comprises essentially a pan forming the bottom of the tank 30 for concentrated solution, and an orifice (not shown) permitting the passage of the dip tube 32. In addition, it comprises channels 44, 45 for the circulation of the fresh dialysis liquid, the housing of the diaphragm pump 35 for the circulation of the dialysis liquid and its valves 35a and 35b, the evacuation channels 22 for the used dialysis liquid and the bottom of the float chamber 37. Finally, it contains the bottom of the bubble trap 27 for the blood.

The bottom flexible element 14 serves in particular a sealing function, especially for the dialysis liquid circuit, being clamped by the bottom element 11 against the elements 10, 12 and (a). In addition, the following orifices are provided in it:

a cutout around the concentrated dialysis solution tank 30, cutouts 44 and 45 enabling the fresh dialysis liquid to flow into the haemodialyser after passing through the bottom element 11, cutouts around the bubble trap 27 and upstream and downstream blood tubes 27a and 27b, cutouts around the tank 37 receiving the used dialysis liquid, and cutouts of orifices 35a and 35b enabling this flexible element to constitute the active portion of the corresponding valves of the pump 35.

Moreover, this flexible element constitutes the diaphragm of the diaphragm pump 35 for the circulation of the dialysis liquid.

The dialysis liquid storage means (e) are formed inside the container 34 by the two compartments 40 and 41 of a supple bag. These compartments may be formed for example from an extruded polyethylene tubular sheath, heat-sealed at both ends and joined to the corresponding orifices and tube connections 32, 44 and 46.

These storage means may preferably be integrated, at least partially, into the said common unit D through the fact that the bottom multifunctional element 11 may constitute the cover of the container 34. The flattened tubular sheath then covers the bottom face of the element 11. This integration may be further increased by the fact that the flattened tubular sheath may advantageously be introduced, together with the flexible element 14, between the rigid or semirigid elements 11 on the one hand, and the elements 10, 12 and (a) on the other hand, while the appropriate corresponding orifices may be made both in the flexible element 11 and in at least one of the walls of the flattened tubular sheath.

The lateral multifunctional element 10 essentially comprises an elongate cavity 30 open at top and bottom, and internally rib partitioned by elements 30a and 30b serving both as baffles and as stiffening elements. It is supported directly on the stack of membranes and intercalated plates forming the haemodialyser (a), by means of a suitably ribbed face. In addition, it comprises an element of the dip tube 32 and a housing for the non-return valve 31a.

The lateral multifunctional element 12 occupies a position substantially symmetrical to the said element 10, in relation to the haemodialyser (a). However, it groups together the majority of the members disposed on the blood circuit and on the used dialysis liquid circuit. Thus, it includes (see also FIG. 10) the arterial tube bringing the blood from the blood entry spigot 21 to the injection zone 23 and thence to the diaphragm pump 24. It includes the body of the pump 24 and the housings corresponding to the upstream and downstream valves 24a and 24b respectively.

On the used dialysis liquid circuit it includes the tube 36 feeding the float chamber 37 from the top orifice 39, the chamber 37 itself, inside which the float 38 is received. The channel 37a brings the top part of the chamber 37 into communication with the atmosphere. The bottom face of the element 12 is grooved so as to form, in cooperation with the bottom elements 14 and 11, the circuits already described. The orifice 35 permits a mechanical connection between the console (h) and the diaphragm of the pump 35 circulating the dialysis liquid.

The elements (g) for removing and measuring amounts of liquid equal (in volume, in weight and/or in flow) to the desired amounts of ultrafiltrate are composed of a tube 47 provided with a supple section 42 adapted to be closed by an external device of any known kind, such as an adjustable screw acting in the direction of the arrow F 42, so as to close the section of the tube 47 to a greater or lesser extent. This tube 47 opens by way of a pouring spout 47a into a graduated vessel 43. The volume of liquid withdrawn is immediately replaced by an equal volume of ultrafiltrate passing through the membrane until the pressure of the dialysis liquid in the haemodialyser is restored in its original value. The artificial kidney according to the example described thus checks the ultrafiltrate by a volumetric method.

The upper flexible element 15 serves in particular a sealing function, particularly on the blood circuit, being clamped by the upper element 13 against the elements 10, 12 and (a).

In addition, it is in particular provided with the following orifices:

(i) a cutout around the tank 30 for concentrated dialysis solution:

(ii) a valve 31a for the introduction of water into the tank 30;

(iii) cutouts 16 and 17 for the introduction and evacuation of the blood into and from the haemodialyser (a);

(iv) orifices 24a and 24b enabling this flexible element to constitute the active part of the corresponding valves of the pump 24;

(v) the orifices 36 and 39 enabling the used dialysis liquid to flow into the top part of the float chamber 37;

(vi) the orifices 27a and 27b corresponding to the blood circuits respectively upstream and downstream of the bubble trap 27; and (vii) the orifice 37a for connecting the float chamber 37 to the atmosphere.

In addition, this flexible element is provided with reinforced sections opposite the injection zones 23 and 26, thus making it possible, when required, to make injections of serum. This flexible element 15 also constitutes the active part of the diaphragm pump 24 for the circulation of the blood, as well as the active part of the pressure pickup 25.

The upper multifunctional element 13 comprises essentially a boss covering the concentrated solution tank 30, a tube 31 for the introduction of water, the two blood spigots 21 and 29, two orifices 23 and 26 corresponding to the injection zones, respectively upstream and downstream of the haemodialyser (a), two orifices 24 and 25 corresponding to the necessary clearance of the membrane at the point corresponding to the blood pump and to the venous pressure connection, and the orifice 37a for connecting the float chamber 37 to atmosphere.

The lower face of the element 13 is grooved so as to form, in cooperation with the bottom elements 12 and 15, the circuits already described and illustrated, in particular, in FIG. 10.

Figure 11:
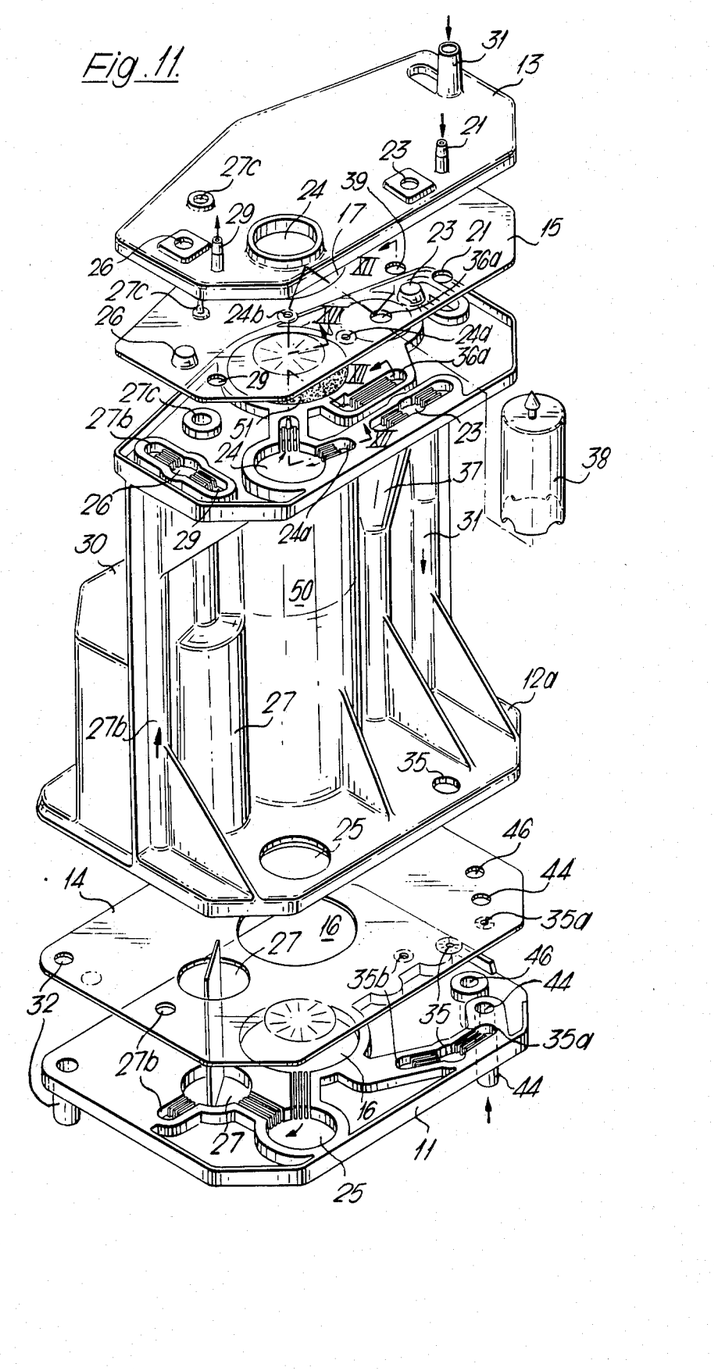
FIG. 11 is an exploded perspective view of another embodiment of the common unit, containing a hollow fibre haemodialyser.

FIG. 11 shows another embodiment of the common integrated unit according to the invention. This unit is distinguished from that shown in FIG. 9 essentially by the fact that it comprises a haemodialyser of the hollow fibre type; in addition, the bundle of hollow fibres is disposed vertically inside a single element 12a which replaces the elements 10 and 12. However, the other flexible elements, such as 14 and 15, or rigid elements, such as 11 and 13, are similar to those shown in FIG. 9. Similarly, the blood and dialysis liquid circulation diagram is of a type comparable with that shown in FIG. 8, the same numerals designating the same or equivalent members serving the same functions.

The element 12a, which is moulded in a single piece, has in its middle portion a cylindrical chamber 50 which is open at its bottom and top ends. A bundle of hollow fibres 51 is inserted into the chamber 50 and projects on both sides. The ends of the hollow fibres are sealed to one another and to the inside walls of the chamber 50, in a manner known per se, by the introduction of a solidifiable resin 52, for example one based on polyurethane compounds, and centrifuging. The two ends of the bundle are then levelled off in the parallel planes of the faces bounding the element 12a, the hollow fibres thus being open at their ends.

Figure 12:
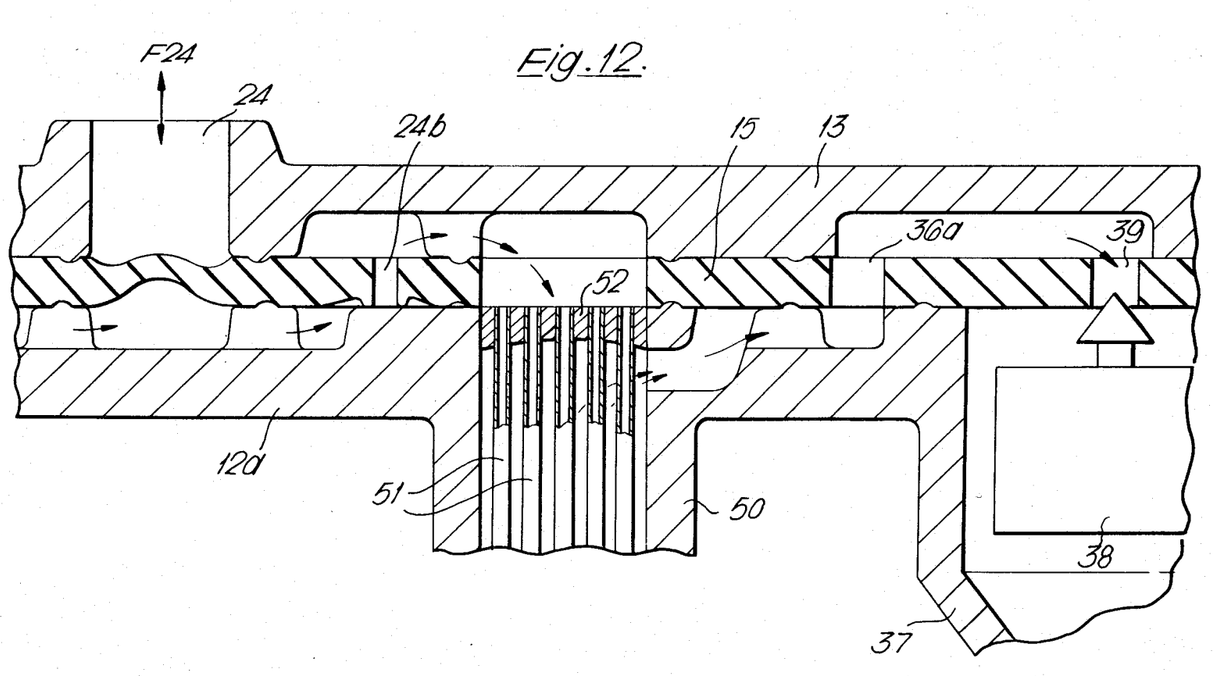
FIG. 12 is a scrap section on the line XII—XII, of FIG. 11.

FIG. 12 illustrates in detail the portions of circuits, through which the blood and the dialysis liquid flow, which are situated near the top end of the hollow fibre haemodialyser. Similar arrangements exist at the bottom end. The blood is pumped by the diaphragm pump 24 driven by the forces F 24 by the action of a motor (not shown) disposed in the console (h), through a nonreturn valve 24b. From the latter it flows to the interior of the hollow fibres constituting the bundle 51.

The dialysis liquid passes through the chamber 50 outside the hollow fibres and countercurrently to the blood, passing out laterally under the potting zone 52 through a channel which conducts it to the orifice 36a, through which it passes and from which it goes through the orifice 39 to reach the float chamber 37. At least a part of the wall of the element 13 delimiting the passage between the orifices 36a and 39 is advantageously of transparent material, cooperating with a colorimeter (not shown) housed in the console (h).

Some modifications are shown in FIG. 11. Thus, the concentrate tank 30 contains no internal baffles 30a or 30b.

Similarly, the means (g) for removing amounts of dialysis liquid equal to the desired amounts of ultrafiltrate are not integrated into the common unit and are therefore not shown here. The valve 27c, which is adapted to be controlled from outside (console h), makes it possible to connect the bubble trap 27 to atmospheric pressure.

It will be observed that the integrated common unit shown in FIG. 11 comprises no more parts than a simple conventional hollow fibre haemodialyser. On each side of the casing 12a containing the bundle of hollow fibres 51, is attached a cover (elements 11 and 13) gripping a gasket (elements 14 and 15 respectively). These elements can be joined together simply by ultrasonic welding after first being positioned.

Referring for example to FIGS. 10 and 12, it can be seen that the common unit D according to the invention comprises at least one flexible element, such as element 15, of plane general shape and relatively thin, which is disposed between the mutually opposite faces of at least two rigid or semirigid elements, such as elements 12, 12a and 13.

All these elements cooperate to form in this way at longitudinal channels of the blood and fresh or used dialysis liquid circuits. These channels can advantageously be connected together by one or more transverse channels, such as the channel 27b provided inside the element 12a (FIG. 11).

Each circuit comprises channels formed in each of the mutually opposite faces and sealingly delimited by the flexible element. The latter is provided with the openings required to permit the passage of the liquid from one face to the other of the flexible element. The channels are advantageously ribbed, with elongate parallel ribs regularly supporting the flexible element, so that an adequate passage is provided for the liquid and at the same time continuous leaktightness is ensured.

The flexible element may be locally thinned to increase its flexibility when it serves as a diaphragm pump, or else reinforced when it constitutes an injection zone, or it may be preshaped when it serves as a non-return valve.

According to the invention, a great diversity of circuits can thus be formed and be disposed in such a manner that they do not intercross. In order to avoid all risk of leakage of a liquid from one of the circuits into another, for example a leakage of blood into the dialysis liquid, they can easily be separated by zones which are connected, directly or otherwise, to the atmosphere (cf. for example the orifices 37a in the elements 13 and 15, FIG. 9).

The artificial kidney according to the present invention may undergo very numerous modifications which are within the competence of the technician. Thus, the elements (a), (b), (c), (d), (e), (f) and (g) having been integrated into one and the same common unit, it is still possible for only some of these elements to be integrated around the means (b) and (d).

For example, it is possible not to integrate the concentrated solution tank 30 into the common unit D, thus achieving a simplification, particularly of the elements 10, 11 and 13. However, the tank 30 can then be integrated into the container 34 to constitute a secondary integrated unit, which is connected to the principal common unit D. An arrangement of this kind may offer advantageous flexibility of use. In addition, the volume of the tank 30 may, if desired, be greater or smaller than the dialysis liquid capacity of the entire circuit.

In addition, accessory devices may be eliminated, modified, or added. Thus, for example, a bubble trap may be added to the blood circuit upstream of the haemodialyser, or a flask of serum may be inserted directly in an injection zone, or a second blood pump may be disposed downstream of the haemodialyser, thus making it possible to regulate the blood pressure in the haemodialyser, and therefore the flow of ultrafiltrate, or else an alternating closure device may be provided for the blood tubes, for use with a single needle.

The degassing of the bubble trap may be automatic or be controlled from the outside, for example controlled in dependence on the maintenance of a substantially constant blood level in this bubble trap, and so on.

In the dialysis liquid circuit it is also possible to replace the float type regulation device by a conventional regulation device comprising a valve connected to a dialysis liquid pressure indicator which keeps the valve of this pressure within predetermined limits. All these means may or may not then be integrated into the common unit D. The dialysis liquid circulating pump 35 may then be disposed downstream of the haemodialyser (a).

It is also possible to replace the obturation device 42 for removing amounts of liquid equal to the desired amounts of ultrafiltrate, with a diaphragm pump flanked by non-return valves of the same type as those already used for displacing the blood or the dialysis liquid, this pump taking advantage of the characteristics of the flexible element 14. A supple bag may also take the place of the graduated vessel 43.

It is also possible to add, for example in the tank 30 which would then no longer serve as concentrate reservoir, cartridges of activated carbon for at least partly purifying the dialysis liquid.

In this case the supple plastic bag inside the container 34 may then comprise only a single compartment.

It is also possible, for example, to add to the dialysis liquid circuit a conductivity meter, a dialysis liquid heating and temperature control device, a water softener, a second dialysis liquid circulating pump for recirculating in the haemodialyser a suitable mixture of fresh dialysis liquid and recycled used liquid.

The haemodialyser may be of any known type. For example, the bundle of hollow fibres may advantageously be divided and distributed into elementary bundles in compartments through which the blood and/or the dialysis liquid flow serially.

The inlet and outlet orifices for the blood and the dialysis liquid may, in the case of a plane membrane haemodialyser, be differently positioned from those shown in FIG. 9.

The independent flexible elements, such as elements 14 and 15, may occupy only a fraction of the section of the common unit D; they may be staggered or situated in non-parallel planes, for example planes at right angles to one another. They are composed of supple, leaktight diaphragms, for example sheets of polyurethane, silicone elastomer, plasticiser polyvinyl chloride, and/or synthetic rubber of a thickness of the order of 0.3 to 3 mm, for example 1 millimeter. They may be produced by moulding.

Accesses from the common unit D to the control and checking console (h) may be provided, as desired, on the top, on the bottom and/or on the sides.

The linkages and/or connections between the flexible elements of the common unit D and the members for controlling and checking grouped together in the console (h) may be of any known type, for example pneumatic or mechanical. The control of the displacement of the flexible element may be of the single or double acting type. For example, metallic inserts adapted to engage (double acting) on control rods driven by motor devices mounted on the console (h) may be housed in the flexible elements. It is also possible for suction cups, the reciprocating movement of which is controlled from the console (h), to be applied to the flexible elements.

The semirigid or preferably rigid elements can be produced by techniques which lend themselves to inexpensive mass production, for example by moulding or injection. They may be produced with two, three or four moulding directions.

In particular, use may be made of all transparent or non-transparent plastics materials capable of being processed by these techniques. Metal inserts may be fitted if desired.

The common unit D is disposable. It could however, optionally be re-used, at least partially, a number of times after sterilisation. The haemodialyser could then be in the form of an interchangeable cartridge which could easily be connected to and disconnected from the remainder of the common unit.

A common unit D of the type shown in FIG. 9, comprising a haemodialyser having a membrane area equal to 0.6 m$^2$ thus weighs only about 1 kg, that is to say the same weight as a haemodialyser of the same type, with a membrane area equal to 1 m$^2$, by itself. The volumes, and therefore the dimensions, are substantially in the same ratios. The present invention in fact makes it possible to reduce by at least 30% the weight of plastics material used for each treatment, if all the necessary accessories are included.

This reflects the considerable simplification made by the present invention both as regards manufacture and as regards transport, storage or use.

The manufacturer in fact uses only very little material, since the latter is used for a multiplicity of purposes. The number of parts is reduced in practice to the number required for the haemodialyser along. This results in simply, easily automated assembly. Furthermore, the multiple functions of the rigid elements result in extensively ribbed shapes, so that they have the rigidity necessary for ensuring excellent retention of the haemodialyser and very good leaktightness of the blood and dialysis liquid circuits.

Furthermore, it is only necessary to use a very small console (h), because the console does not need to include any part of the dialysis liquid circuit, any means enabling preheated, softened water to be obtained, or a container to hold the dialysis liquid. For each session he uses a common unit D which includes all the necessary complementary equipment and which he generally discards after use, in order to have the benefit of the best conditions of sterility.

Thus, apart from its economy, the considerable lightening of the equipment required, its convenience and its simplicity of use, together with its substantially improved reliability and safety, make the artificial kidney according to the invention a kidney particularly suitable for the requirements of treatment at home.

We claim:
1. In an artificial kidney comprising, in combination, the following elements:
   (a) a haemodialyzer including:
      (i) a membrane which is capable of permitting the treatment of blood, particularly by dialysis and by ultrafiltration, said membrane dividing the haemodialyzer into first and second compartments;
      (ii) means for feeding blood to and from the first compartment; and
      (iii) means for feeding the dialysis liquid to and from the second compartment;
   (b) an extracorporal blood circuit through which the blood passes outside the haemodialyser from the patient to the blood feeding means of the haemodialyzer;
   (c) means for preparing the dialysis liquid, ready for circulation into a dialysis liquid circuit through said second compartment;

(d) means for causing the dialysis liquid to circulate through said second compartment into said dialysis liquid circuit;
(e) means for regulating the pressure of the dialysis liquid in said haemodialyzer;
(f) storage means for storing the fresh and/or used dialysis liquid
(g) means for removing and measuring amounts of dialysis liquid equal to the desired amounts of ultrafiltrate and
(h) means for controlling and checking, in particular, the elements (b) and (d),
the improvement comprising,
two independent flexible elements of generally thin planar shape, provided with apertures for liquids, and located on opposite parts of the haemodialyzer,
at least one rigid or semi-rigid multifunctional element provided with apertures for liquids, located internally between the flexible elements, in association with the haemodialyzer,
two other rigid or semi-rigid multifunctional elements, one of which is located external of each of the flexible elements,
the rigid or semi-rigid multifunctional elements contain within themselves the extracorporal blood circuit and the dialysis liquid circuit, the flexible elements performing all sealing functions.

2. The artificial kidney as claimed in claim 1, wherein the two flexible elements are disposed in substantially parallel planes on each side of the internal rigid or semi-rigid multifunctional elements and the haemodialyzer, and wherein at least two of the rigid or semi-rigid multifunctional elements comprise mutually opposite faces which cooperate to form at least a part of the extracorporal blood circuit and the dialysis liquid circuit, each circuit consisting essentially of channels provided in each of the mutually opposite faces, the two flexible elements disposed separately between the mutually opposite faces, the channels being sealingly delimited by the flexible elements.

3. The artificial kidney as claimed in claim 1, wherein a concentrate reservoir is comprised within at least one of the rigid or semi-rigid multifunctional element, the reservoir being provided with two pipes for connection, respectively with an upstream source of fresh water and with a downstream dialysis liquid storage container.

4. An artificial kidney as claimed in claim 1, wherein the two flexible elements are in cooperation with the mutually opposite faces provided with channels of the adjacent rigid or semi-rigid multifunctional elements. The liquid circuits having longitudinal portions, at least two of which are connected together by at least one transverse passage provided inside at least one of the rigid or semi-rigid multifunctional elements.

5. An artificial kidney as claimed in claim 1, wherein the extracorporal blood circuit and the dialysis liquid circuit are separated from one another by zones connected to the atmosphere.

6. An artificial kidney as claimed in claim 1, comprising a haemodialyzer provided with generally flat membranes set between parallel spacers, the haemodialyzer being pressed between two of the internal rigid or semi-rigid multifunctional elements, the first one comprising at least a major part of the concentrate reservoir and the second one comprising most of the extracorporal blood circuit and of the dialysis liquid circuit.

7. An artificial kidney as claimed in claim 1, comprising a haemodialyzer provided with a bundle of hollow fibers, inside a single internal rigid or semi-rigid multifunctional element, whose each of the two parallel opposed faces are bonded respectively, through each of the flexible elements to each of the external rigid or semi-rigid multifunctional elements.

* * * * *